US012708506B2

(12) United States Patent
Levon et al.

(10) Patent No.: US 12,708,506 B2
(45) Date of Patent: Aug. 18, 2026

(54) SYSTEM AND METHOD FOR IMPLANT PRODUCTION

(71) Applicant: NEW YORK UNIVERSITY, New York, NY (US)

(72) Inventors: Kalle Levon, Brooklyn, NY (US); Freya Schnabel, New York, NY (US); Nolan Karp, New York, NY (US); Vittoria Flamini, Brooklyn, NY (US)

( * ) Notice: Subject to any disclaimer, the term of this patent is extended or adjusted under 35 U.S.C. 154(b) by 1093 days.

(21) Appl. No.: 17/560,916

(22) Filed: Dec. 23, 2021

(65) Prior Publication Data

US 2022/0202560 A1 Jun. 30, 2022

Related U.S. Application Data

(60) Provisional application No. 63/130,484, filed on Dec. 24, 2020.

(51) Int. Cl.
*A61F 2/12* (2006.01)
*B33Y 10/00* (2015.01)
(Continued)

(52) U.S. Cl.
CPC ................ *A61F 2/12* (2013.01); *B33Y 10/00* (2014.12); *B33Y 50/00* (2014.12); *B33Y 80/00* (2014.12); *G06T 7/30* (2017.01); *A61F 2240/004* (2013.01); *G06T 2207/10048* (2013.01); *G06T 2207/10081* (2013.01);
(Continued)

(58) Field of Classification Search
CPC ..... A61F 2/12; A61F 2240/004; B33Y 10/00; B33Y 50/00; B33Y 80/00; G01T 7/30; G01T 2207/10048; G01T 2207/10081; G01T 2207/10088; G01T 2207/10136; G01T 2207/30052
See application file for complete search history.

(56) References Cited

U.S. PATENT DOCUMENTS 5,545,217 A * 8/1996 Offray ...................... A61F 2/12 623/8
6,432,138 B1 * 8/2002 Offray ...................... A61F 2/12 623/8

(Continued)

OTHER PUBLICATIONS

Hemmingsen, M.N., Larsen, A., Ørholt, M. et al. 3D Imaging Versus MRI for Measuring Breast Volume: What is the Evidence?. Aesth Plast Surg 43, 554-555 (2019). https://doi.org/10.1007/s00266-018-1288-6.

(Continued)

*Primary Examiner* — Nahida Sultana
(74) *Attorney, Agent, or Firm* — Riverside Law LLP

(57) ABSTRACT

Disclosed herein is a multi-modal imaging methodology for creating patient-specific three-dimensional images of a breast volume, for use in the production of breast implants. In one aspect, a surface imaging technique may be used to create a three-dimensional model of an external shape of a patient, such as the external morphology of a breast. In one aspect, an internal imaging technique may be used to create a three-dimensional model of the internal shape of the thorax underneath the breast. The external and internal models may then be referenced to one another and a unified model may be created to generate a reliable, personalized model of breast volume.

17 Claims, 10 Drawing Sheets

(51) Int. Cl.
*B33Y 50/00* (2015.01)
*B33Y 80/00* (2015.01)
*G06T 7/30* (2017.01)

(52) U.S. Cl.
CPC ............... *G06T 2207/10088* (2013.01); *G06T 2207/10136* (2013.01); *G06T 2207/30052* (2013.01)

(56) References Cited

U.S. PATENT DOCUMENTS 7,520,896 B2 * 4/2009 Benslimane .......... A61F 2/0095 623/7
8,781,557 B2 * 7/2014 Dean .................. A61F 2/30942 128/923
8,795,204 B2 8/2014 Mordaunt
9,008,382 B2 4/2015 Highnam
9,114,003 B2 * 8/2015 Kalus ........................ A61F 2/12
10,895,020 B2 * 1/2021 Krieger .................. B33Y 50/00
11,304,812 B1 * 4/2022 Khalid .................. A61F 2/2875
11,564,793 B2 * 1/2023 Baek ....................... A61F 2/186
2003/0023266 A1 * 1/2003 Borillo ............. A61B 17/12172 606/200
2006/0228015 A1 * 10/2006 Brockway ............. G06T 7/0012 382/132
2007/0293752 A1 * 12/2007 Simpkin ................ A61B 5/442 600/407
2009/0147073 A1 6/2009 Getty
2009/0219289 A1 * 9/2009 Kalvin .................... G06T 19/00 345/427
2013/0238096 A1 * 9/2013 Kotlus .................... A61F 2/442 29/592
2014/0094924 A1 * 4/2014 Hacking ............... A61F 2/4261 29/592
2016/0235380 A1 8/2016 Smith
2016/0371835 A1 * 12/2016 Grbic ..................... A61B 34/10
2017/0057169 A1 * 3/2017 Grbic .................... A61F 2/2415
2018/0008220 A1 1/2018 Boone
2018/0064530 A1 * 3/2018 Glicksman ................ A61F 2/12
2019/0000318 A1 1/2019 Caluser
2019/0117379 A1 4/2019 Quirós
2019/0167183 A1 6/2019 Shia
2020/0178936 A1 * 6/2020 Padwal ................ A61B 5/4312
2021/0263498 A1 * 8/2021 Bandara ................. B33Y 50/00

OTHER PUBLICATIONS

House, Rachael Marie. “Breast Reconstruction Planning and Assessment Using Three-Dimensional Surface Scans.” Queen’s University, 2019 (pp. 1-74).

O’Connell, R.L., Khabra, K., Bamber, J.C. et al. Validation of the Vectra XT three-dimensional imaging system for measuring breast volume and symmetry following oncological reconstruction. Breast Cancer Res Treat 171, 391-398 (2018). https://doi.org/10.1007/s10549-018-4843-6.

R.M. Lacher, F. Vasconcelos, N.R. Williams, G. Rindermann, J. Hipwell, D. Hawkes, D. Stoyanov, Nonrigid reconstruction of 3D breast surfaces with a low-cost RGBD camera for surgical planning and aesthetic evaluation, Medical Image Analysis, vol. 53, 2019, pp. 11-25, ISSN 1361-8415, https://doi.org/10.1016/j.media.2019.01.003.

Three-dimensional Assessment of the Breast: Validation of a Novel, Simple and Inexpensive Scanning Process Carlo M. Oranges, Srinivas Madduri, Philipp Brantner, Bilal Msallem, Salvatore Gi Rdano, Benito Benitez, Daniel F. Kalbermatten, Dirk J. Schaefer, Florian M. Thieringer In Vivo May 2019, 33 (3) 839-842; DOI: 10.21873/invivo.11548.

Wang, C., Luan, J., Cheng, H. et al. Menstrual Cycle-Related Fluctuations in Breast Volume Measured Using Three-Dimensional Imaging: Implications for Volumetric Evaluation in Breast Augmentation. Aesth Plast Surg 43, 1-6 (2019). https://doi.org/10.1007/s00266-018-1243-6.

* cited by examiner

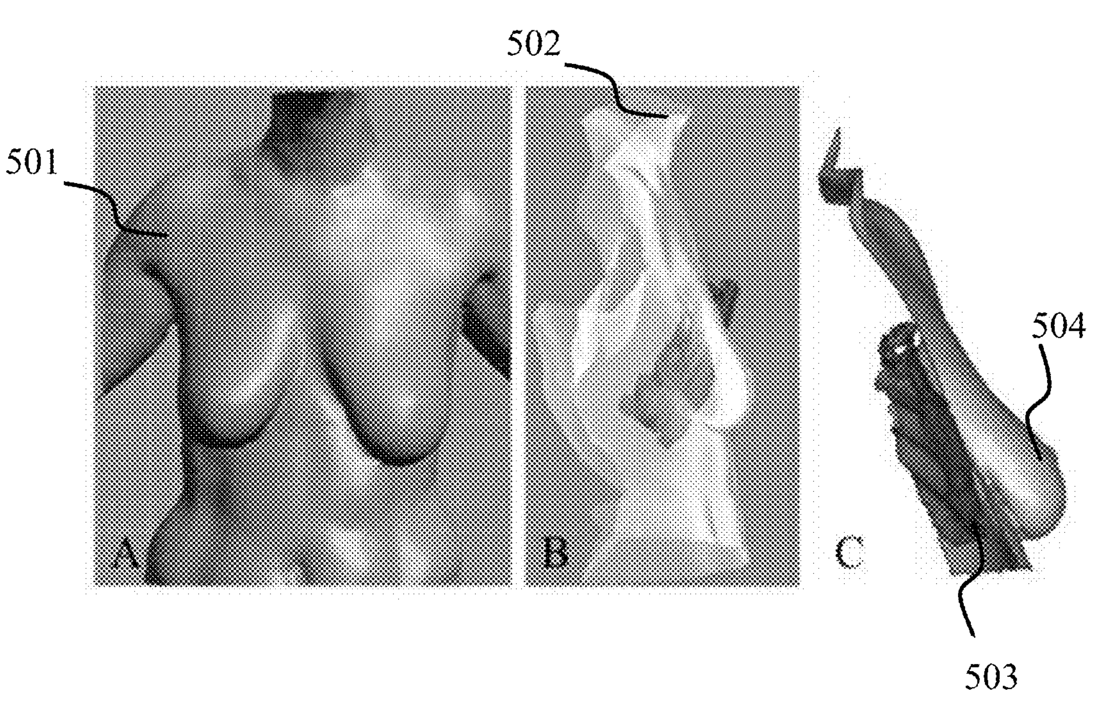
Fig. 5A
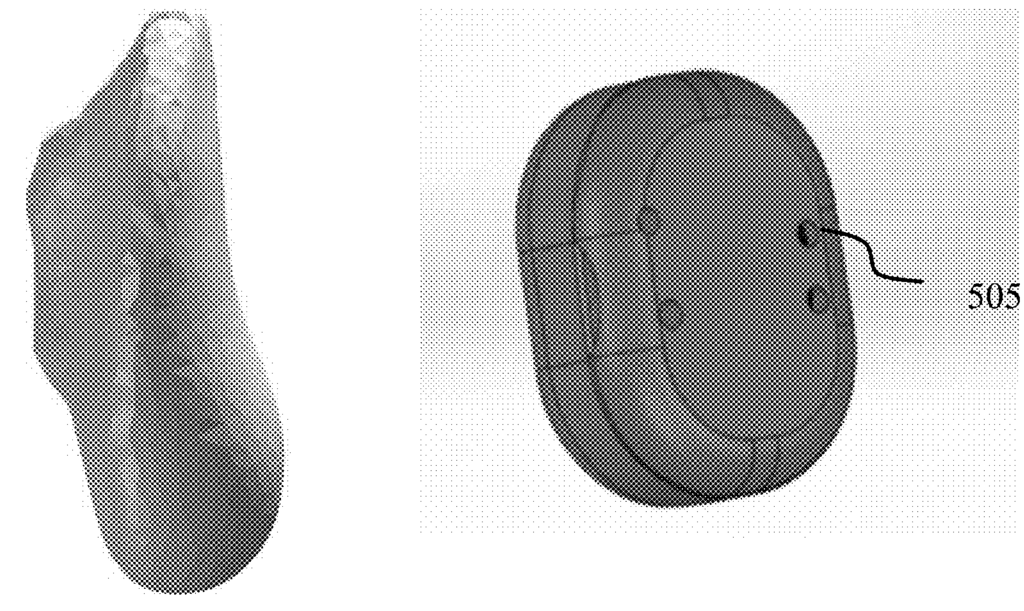
Fig. 5B
Fig. 5C

SYSTEM AND METHOD FOR IMPLANT PRODUCTION

CROSS-REFERENCE TO RELATED APPLICATIONS

This application claims priority to U.S. Provisional Application No. 63/130,484, filed on Dec. 24, 2020, incorporated herein by reference in its entirety.

BACKGROUND OF THE INVENTION

Each year about 250,000 new cases of breast cancer (BC) are diagnosed in the US. Of these new cases, approximately 20% are diagnosed in women aged younger than 50 years and 43% occur among women who are aged 65 years and older. The overall 5-year relative survival rate for patients with BC has improved from 74.8% in the late 1970s to 90.3% in 2009, and 15-year relative survival rate is 77.8%. Around 40% of all BC patients undergo either UM or BM. Given the improved life expectancy in these patients and the relative young age of the diagnosis, it is important to offer breast reconstruction (BR) options that match patient expectations. Pre-menopausal women that test positive at genetic screening for highly penetrant BC genes such as BRCA 1 and 2, are also offered to undergo BM as a prophylactic measure to drastically reduce the chance of disease occurrence.

Current options for implant production, including breast reconstruction (BR) are reconstruction using standard-shaped implants, which in BR includes silicone implants (SI), or autologous fat transfer from the abdomen. While autologous fat transfer is limited by the amount of abdominal fat available and by the ability of the operating plastic surgeons to create a precise match with the original tissue by hand, BR with off-the-shelf SIs is predictable and repeatable. However, SIs are available only in two shapes, round or teardrop (also called anatomical), which rarely match patients' pre-operative breast shape (see FIG. 1). The lack of a variety of SI shapes is a major limitation to post-operative emotional wellbeing and aesthetic satisfaction in patients.

Breast volume is defined by the space between two surfaces: an external one, the skin, and an internal one, the pectoralis major. Conventional imaging approaches for breast reconstruction, based on 3D scanners, can determine with great accuracy the external surface, but the internal surface, which drapes over the ribcage and has curves and ridges specific to each patient, cannot be easily determined.

In scientific literature several attempts at achieving a reliable description of breast volume based on multimodal images are described, but have failed in producing a good approximation of the breast volume due to the fact that most clinical breast imaging procedures are obtained through a deformation of breast tissue, whether by compression, in mammograms, or by acquiring images in the prone position, in breast MRIs. Moreover, each of these imaging techniques, whether using x-rays or magnetic fields, focuses the image contrast on tissues with different densities, thus complicating the identification of shared landmarks between clinical images. Some investigators have tried to combine ultrasounds acquisitions with clinical MRI data, but on top of the difficulty of registering ultrasounds acquisitions, which are operator dependent, such datasets combine breast volumes acquired in the supine position with breast volumes obtained in the prone position, neither of which correspond to the shape of the breast in the standing position, which is the most common orientation of the breast.

Currently produced SIs are made in limited standard shapes in part because they are made from curable materials which must be shaped in molds, which are expensive and time consuming to produce. Advances in additive manufacturing in recent years allow for low-cost, faster production of customized parts. Additionally, some reports suggest that current materials used in SIs may lead to complications or other medical issues, for example some materials may be linked to increased incidence of anaplastic large-cell lymphoma.

Thus, there is a need in the art for a new method for designing and producing implants with new innovative materials using multi-modal imaging and additively manufactured molds in order to quickly and efficiently produce safe, patient-specific implants. The present invention satisfies this need.

SUMMARY OF THE INVENTION

In one aspect, the present invention relates to a method for designing an implant for a subject, comprising: obtaining at least one internal image of an internal anatomy of the subject, the at least one image comprising at least one internal view of an anatomical landmark; obtaining at least one surface image of a surface of the subject, the at least one external view of the anatomical landmark; generating an internal three-dimensional model of the internal anatomy of the subject from the at least one internal image; generating an external three-dimensional model of the surface of the subject from the at least one surface image; registering the internal three-dimensional model to the external three-dimensional model with the anatomical landmark to create a unified three-dimensional model of the subject; calculating an implant shape from a void in the unified three-dimensional model; and creating a three-dimensional model of an implant having the implant shape.

In one embodiment, the implant is a breast implant. In one embodiment, the at least one internal view comprises the pectoralis major.

In one embodiment, the method further comprises the steps of: segmenting the pectoralis major; and calculating a thickness of the pectoralis major.

In one embodiment, the anatomical landmark is selected from the group consisting of the sternum, the suprasternal notch, and a side of a ribcage. In one embodiment, the breast implant is a prepectoral breast implant. In one embodiment, the breast implant is a subpectoral breast implant. In one embodiment, the at least one internal image is generated by a method selected from the group consisting of MRI, X-Ray, and Ultrasound. In one embodiment, the at least one surface image is generated by a method selected from the group consisting of a 3D scanner, stereoscopic imaging, millimeter-wave imaging, and infrared imaging.

In one embodiment, the method further comprises the step of creating the implant with an additive manufacturing process. In one embodiment, the method further comprises the steps of: creating a three-dimensional model for a mold from the calculated implant shape; and building the mold from the three-dimensional model; and forming the implant with the mold.

In one embodiment, the mold is built using an additive manufacturing process. In one embodiment, the method further comprises the steps of forming a replica of the implant with the mold; and forming the implant from the replica. In one embodiment, the implant comprises a first material, and the method further comprises the step of coating the implant with a second material different from the first material.

In one embodiment, the method further comprises the step of creating the implant, wherein the implant comprises an alginate hydrogel. In one embodiment, the alginate hydrogel is a 1% wt alginate hydrogel. In one embodiment, the alginate hydrogel comprises sodium alginate.

In one aspect, the present invention relates to system for designing an implant for a subject, comprising a computing device comprising a non-transitory computer-readable medium with instructions stored thereon, which when executed by a processor perform steps comprising: generating an internal three-dimensional model of an internal anatomy of the subject from at least one internal image of the internal anatomy of the subject; generating an external three-dimensional model of a surface of the subject from at least one surface image of the subject; registering the internal three-dimensional model to the external three-dimensional model with an anatomical landmark present in the internal three-dimensional model and the external three-dimensional model; calculating an implant shape from a void in the unified three-dimensional model; and creating a three-dimensional model from the implant shape.

In one embodiment, the three-dimensional model is a three-dimensional model for a mold. In one embodiment, the implant is a breast implant. In one embodiment, the at least one internal image is generated by a method selected from the group consisting of Mill, X-Ray, and Ultrasound. In one embodiment, the at least one surface image is generated by a method selected from the group consisting of a 3D scanner, stereoscopic imaging, millimeter-wave imaging, and infrared imaging.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5A, FIG. 5B, and FIG. 5C show different steps of a method of designing and producing implants;

DETAILED DESCRIPTION

Figure 1:
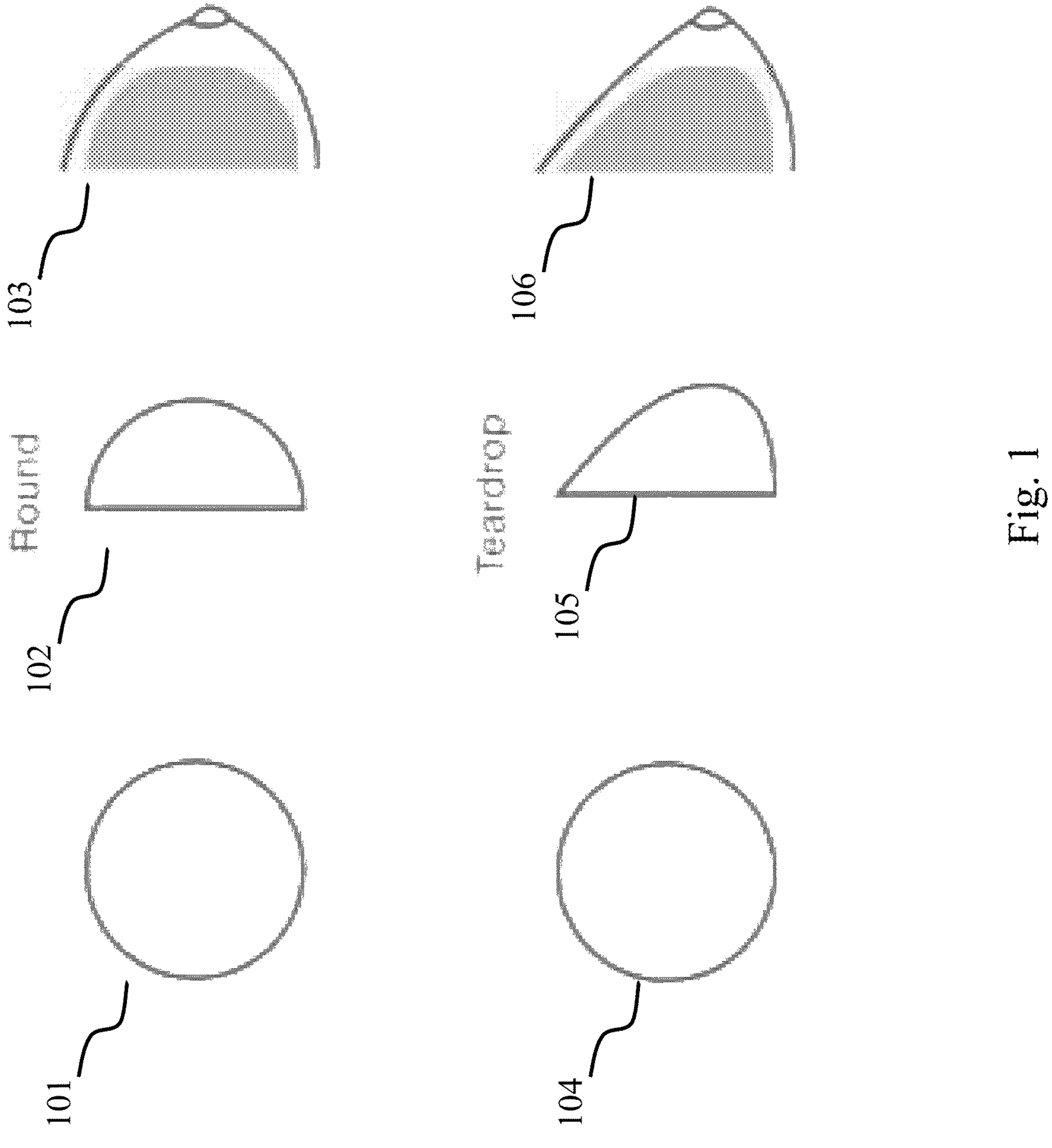
FIG. 1 is an illustration of different types of implants.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Some aspects of the present invention may be made using an additive manufacturing (AM) process. Among the most common forms of additive manufacturing are the various techniques that fall under the umbrella of "3D Printing", including but not limited to stereolithography (SLA), digital light processing (DLP), fused deposition modelling (FDM), selective laser sintering (SLS), selective laser melting (SLM), electronic beam melting (EBM), and laminated object manufacturing (LOM). These methods variously "build" a three-dimensional physical model of a part, one layer at a time, providing significant efficiencies in rapid prototyping and small-batch manufacturing. AM also makes possible the manufacture of parts with features that conventional subtractive manufacturing techniques (for example CNC milling) are unable to create.

Suitable materials for use in AM processes include, but are not limited to, using materials including but not limited to nylon, polyethylene terephthalate (PET), acrylonitrile butadiene styrene (ABS), resin, polylactic acid (PLA), polystyrene, and the like. In some embodiments, an AM process may comprise building a three dimensional physical model from a single material, while in other embodiments, a single AM process may be configured to build the three dimensional physical model from more than one material at the same time.

Disclosed herein is a multi-modal imaging methodology for creating patient-specific three-dimensional images of a breast volume, for use in the production of breast implants. Specifically, in one embodiment, a 3D scanner or other surface imaging technique is first used to create a three-dimensional model of an outer surface of a patient, specifically the external morphology of a breast. An MM or other internal imaging technique may then be used to create a three-dimensional model of the shape of the thorax underneath the breast. In some embodiments, the three-dimensional model of the shape of the thorax underneath the breast may comprise a Digital Imaging and Communications in Medicine (DICOM) file. The internal and external models may then be referenced to one another and a unified model may be created from the two component models, the unified model including an accurate three-dimensional representation of the volume formed by existing breast tissue positioned between the underlying muscular and/or skeletal structure and the surface of the skin.

Although certain embodiments of the disclosed method include the use of a 3D scanner for surface imaging, other surface imaging techniques may be used, including but not limited to stereoscopic imaging, millimeter-wave imaging (sometimes referred to as THz imaging), infrared imaging, and the like. Similarly, although certain embodiments of the disclosed method recite the use of MM imaging as an internal imaging technique, other internal imaging techniques may be used, including X-Ray, ultrasound, and the like. Surface images may be recorded for example as three-dimensional image files, including but not limited to OBJ or STL files.

By performing a multi-modal image registration between the morphological scanning of patients standing in front of a 3D scanner and breast MRIs datasets achieved through custom coding, it is possible to generate a reliable, personalized model of the breast volume. In one embodiment, a method may include the step of marking points of reference on an image acquired from a 3D scanner that correspond to bony points that can be identified also on MRI datasets, such as the sternum, the suprasternal notch, and the sides of the ribcage. Other-widely used skin landmarks, such as the nipple area, cannot be considered as reliable markers due to the extreme changes in shape between these two image acquisition methods.

Clinical breast MRI may not give direct information on the shape of the ribcage due to the poor contrast of bones in breast MM sequences. In one embodiment, the disclosed method relies on the segmentation of the pectoralis major muscle, which drapes the ribcage and is immediately below the breast tissue. Identifying the pectoralis major and its thickness is an advantage of one embodiment of the disclosed method, as it allows for sizing personalized implants for either subpectoral or prepectoral implantation.

Figure 2:
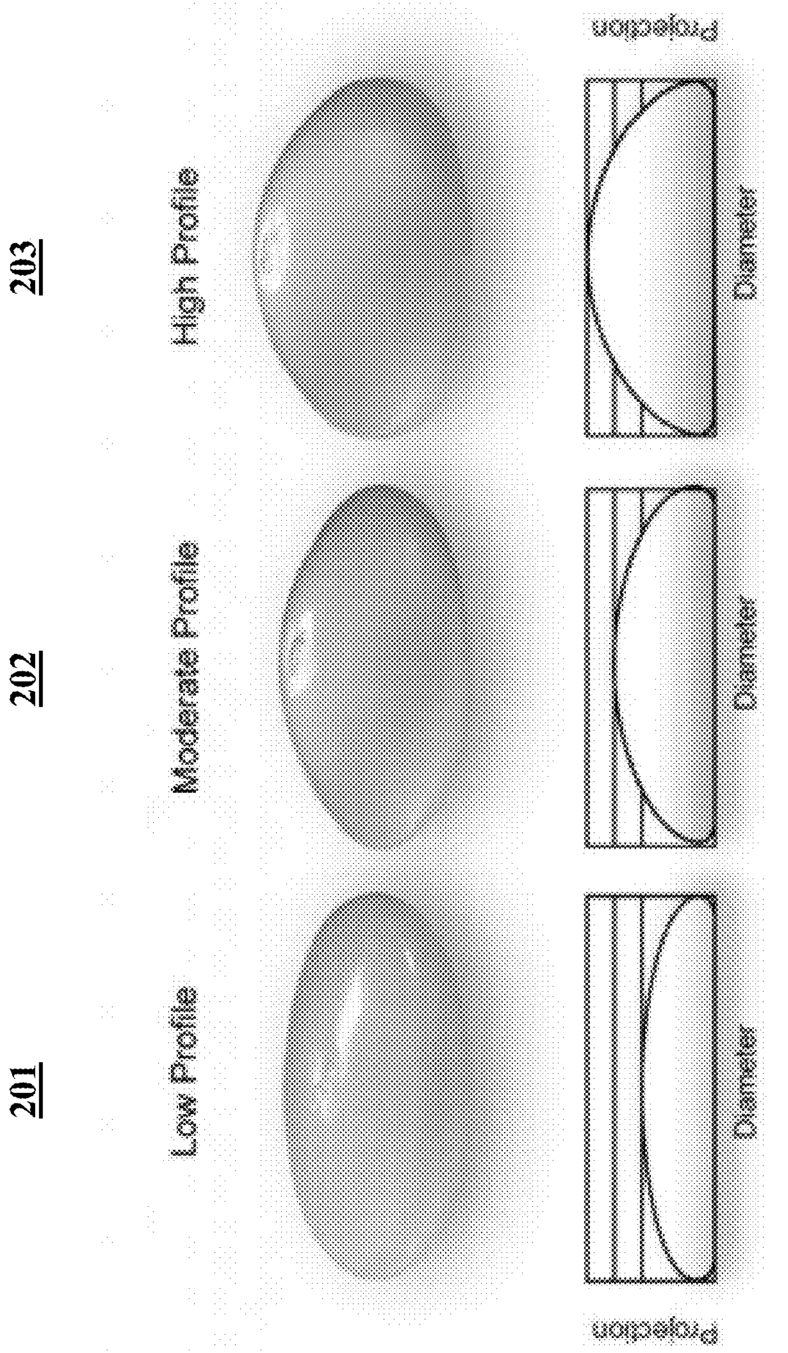
FIG. 2 is an illustration of different types of implants.

An illustration of currently used implants is shown in FIG. 1, FIG. 2, FIG. 3, FIG. 4A, and FIG. 4B. With reference to FIG. 1, the two basic shapes of silicone breast implants are shown. A front view of a round implant is shown in 101, a profile view of a round implant is shown in 102, and an implanted profile view of a round implant is shown in 103. Similarly, a teardrop implant is shown in front view 104, profile view 105, and implanted profile view 106. Standard-shape implants may be made in a range of profiles, as shown in FIG. 2, including for example low profile 201, moderate profile 202, and high profile 203 to allow for some variation in implant size relative to a patient's anatomy.

Figure 3:
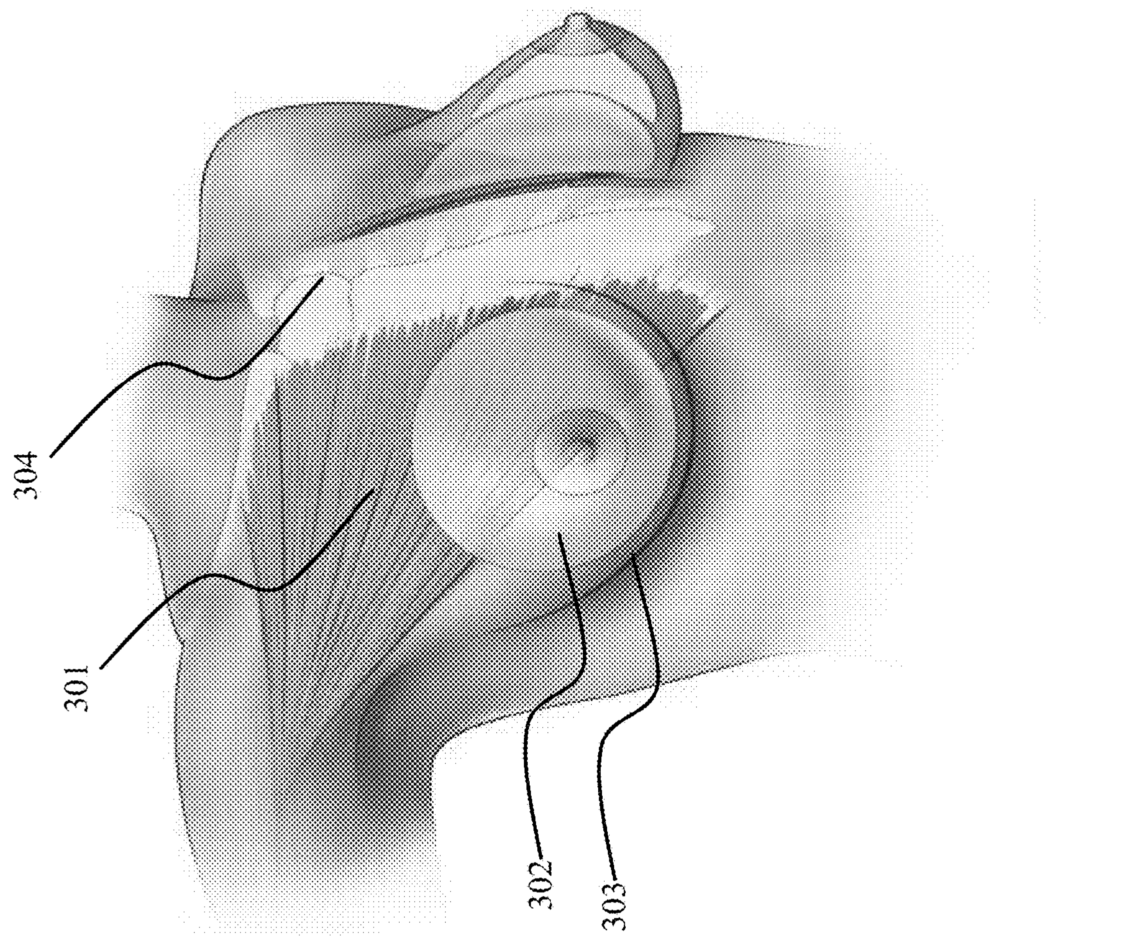
FIG. 3 is an illustration of implanted breast implants.

A view of exemplary round implants is shown in FIG. 3, illustrating the internal and external geometry of the patient which, in conjunction with the implant shape, dictates the outward appearance of the breast once the implant is in place. The shape of the breast depends not only on the size and shape of the implant 302 and the skin 303, but also the shape of the ribcage 304 and pectoral muscle 301 beneath the surface of the skin, on which the implant 302 rests.

Figure 4B:
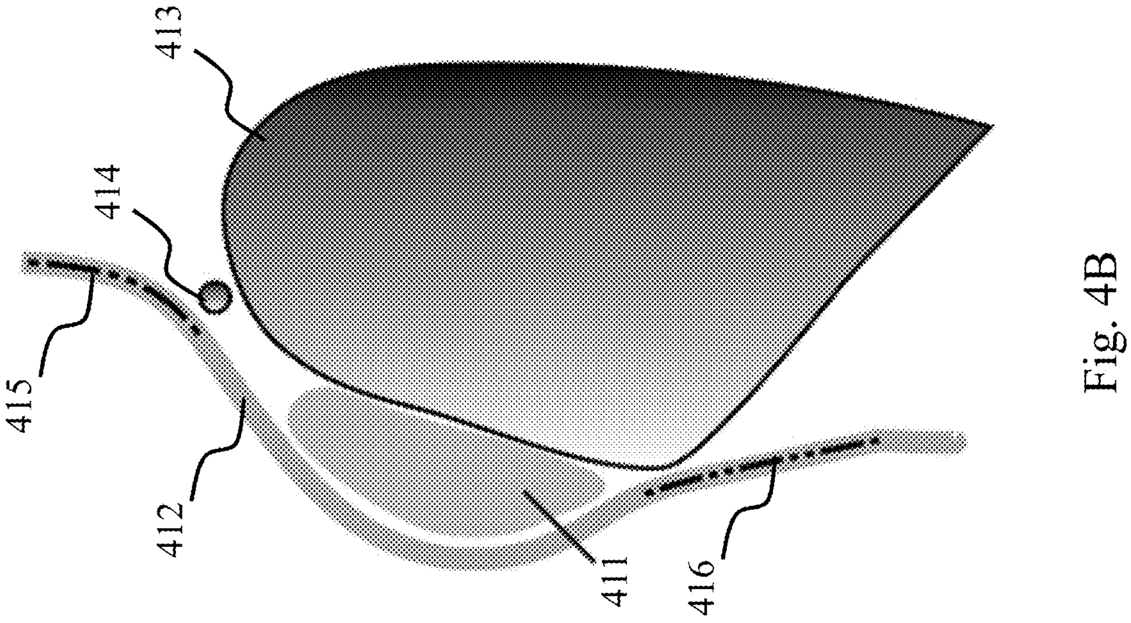
FIG. 4A and FIG. 4B are cross-sectional views of implanted breast implants.
Figure 4A:
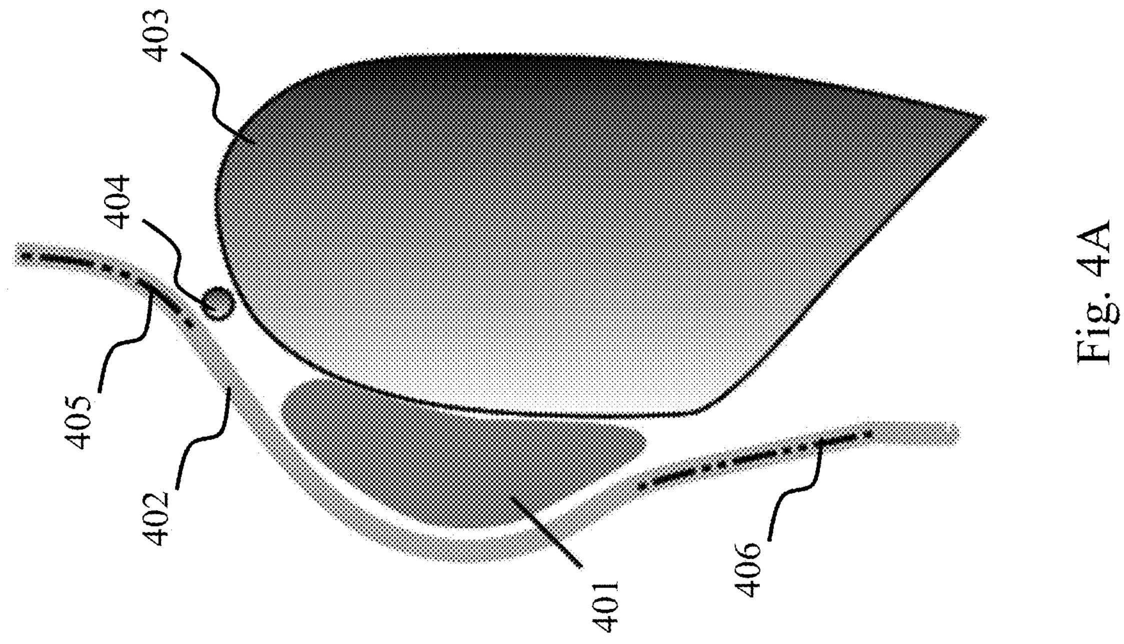

A further illustrative example is shown in FIG. 4A and FIG. 4B. FIG. 4A and FIG. 4B show how given a similar skin geometry (402 is similar to 412) retrieved from an external imaging device, different thoracic geometries may be present (ribcage 403 and clavicle 404 in FIG. 4A differ from ribcage 413 and clavicle 414 in FIG. 4B), as well as breast volume, and therefore a conforming breast implant will have a dissimilar shape (breast volume 401 differs from breast volume 411, even though skin geometry 402 is similar to skin geometry 412).

In one embodiment, the profile line of the skin geometry (402 and 412) is obtained via a 3D scanner, while the dashed lines (405, 406, 415, 416) are obtained via breast MRI. In some embodiments, the profile 402 and the MRI geometry 405 and 406 may be registered to each other as one step of a method to determine the shape of the breast volume 401.

One embodiment of a method of the disclosure is described below. First, a 3D scan may be performed. In one embodiment, a 3D scanner dataset consists of three images (right side, front, left side) and one data file (for example an OBJ file) containing the geometric description of the skin of the patient. In some embodiments, the three images are not used in this invention, and only the geometrical information contained in the data file (OBJ file) is used. In some embodiments, a three-dimensional representation may be constructed from three or more images, and the resulting three-dimensional representation may be used. In one embodiment, a file containing a three-dimensional representation (for example the OBJ file) is then post processed so that anatomical landmarks, such as the sternum, the suprasternal notch, and the sides of the ribcage, can be identified and used as points of reference.

In some embodiments, a method includes obtaining a breast MRI. A clinical breast MM protocol may include the use of a contrast agent, for example gadolinium, and fat saturated sequences. In one embodiment, blood vessels and pathologies with high vascularity appear bright on T1 weighted fat saturated post gadolinium images. In one embodiment, a breast MRI procedure comprises one fat saturated measurement prior to the injection of gadolinium (T1 FS Pre) and five measurements at 45 second intervals after the injection of gadolinium (T1 FS Post). In one embodiment, for the evaluation of the breast volume, two measurements are used, the T1 FS Pre is used to retrieve the morphology of the pectoralis major, as these images offer a good contrast between breast fat tissue (dark) and muscle tissue (grey). The first T1 FS Post may be used to retrieve the morphology of the skin while the patient is lying in the prone position in the MRI.

After the images are acquired, one disclosed method includes the steps of processing one or more images with an algorithm executed on a computing device. MRI measurements may be segmented using a segmentation algorithm, for example a trainable segmentation algorithm based on WEKA classifiers. The muscle measurement and the skin measurement may then be stored as binary images in separate files.

Next, an algorithm registers the skin geometry segmented from the MM images with the skin geometry obtained from the 3D scanner. The reference points (for example the sternum and the suprasternal notch, and the sides of the ribcage) are identified on both images and for each of these landmarks a normal vector is identified. Starting with the suprasternal notch, the rotation matrices necessary to align the two geometries are calculated, and the skin geometry from the 3D scanner is aligned with the skin geometry obtained from the Mill images. The algorithm then matches the skin geometry from the 3D scanner with the muscle geometry obtained from the Mill and calculates the volume needed to fill the space between these two geometries. In the case of a prepectoral implantation, the distal surface of the muscle is used, while the proximal surface of the muscle is used to generate a geometry for a subpectoral implantation. In some embodiments, this is done for one breast at a time to ensure optimal match between the calculated breast volume and the original breast volume. In some embodiments, there may be points at which the adipose layer of a patient is so thick that the distance between the skin geometry and the muscle geometry is larger than 0.5 cm. In some such embodiments, a spline interpolation is used to close the volume, which otherwise is closed using a linear interpolation. At this stage, the breast volume may be stored as a three-dimensional representation, for example a point cloud which describes the breast volume's surface. This point cloud is further interpolated to create a triangulation which results in a watertight STL file that describes the breast volume and can be used to produce personalized breast implants.

The disclosed multimodal imaging method has two key advantages over existing modalities for breast implant design and production. First, the method uses two different imaging modalities, one where the breast is in its natural, standing position, and one in which the body is prone, but the details of the pectoralis major can be seen in great detail. The first advantage is that the breast volumes reconstructed using this approach will look much more similar to the native breast. In particular, using the disclosed method, the distal portion of the implants will mimic the external surface of the breast as reconstructed from the 3D scanner images, while the proximal portion of the implant will sit correctly against the ribcage as its profile will be dictated by the morphology of the pectoralis major.

The second key advantage arises from the use of a breast Mill for reconstruction of the internal surface: Due to the poor contrast of bones in breast Mill sequences; this invention relies on identification of the pectoralis major and its thickness. This is an advantage of the invention, as it allows for the breast volume to be reconstructed for either subpectoral or prepectoral implantation.

Figure 5D:
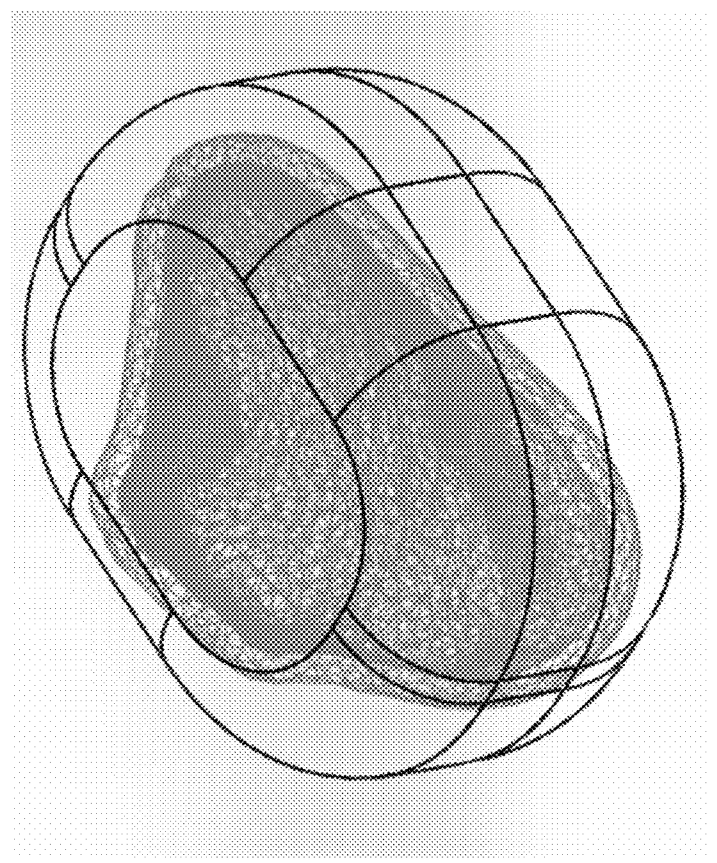
FIG. 5D is an illustration of a mold for an implant.

An exemplary method of the invention is shown with reference to FIG. 5A-FIG. 5D. FIG. 5A shows the three imaging steps, where first a surface image is acquired via 3D scanning in step 501, then an MM image is acquired in step 502. The two images are then registered to one another, and a breast volume is calculated based on the spacing between a portion of the surface image 504 and the registered MM image 503. This volume is then used to construct a three-dimensional model of the breast volume, which may first be in the form of a point cloud but may be represented as a solid volume, as shown in FIG. 5B.

The solid volume from FIG. 5B may either be additively manufactured directly using an additive manufacturing process configured to achieve the desired tolerances with a medically approved material, or may alternatively be used to create a mold via additive manufacturing, like the ones shown in FIG. 5C and FIG. 5D. The mold may be configured with a first half and a second half separated by a cutting plane, shaped to form a quantity of medically suitable material into the appropriate shape. In some embodiments, the cutting plane of the mold is positioned parallel with the breast model where the breast model has the largest surface area. In some embodiments, the mold may include one or more inlets 505 for pouring uncured or liquid material into the mold prior to a curing or hardening process. In such embodiments, the two halves of the mold may then be separated after curing to reveal the finished implant. In other embodiments, the mold may be additively manufactured as a single piece. The single piece mold may include break-away sections, for example sections that are thinner or less dense than surrounding sections, to support destruction and removal of the mold once curing/solidification is complete. In some embodiments, an additively manufactured replica, for example comprising PDMS, is used to create a mold using various processes, and the mold may be filled with medical grade material to create an implant.

In some embodiments, a mold is used to create a replica of an implant, and the replica may be made from, for example, silicone. In some embodiments, the replica is used to create an implantable device using medical grade silicone. In some embodiments, an implantable device may comprise a silicone coating comprising a first material and a silicone filling comprising a second material. In one example, the silicone coating may comprise NuSil MED-6400 silicone. In one example, the silicone filling may comprise NuSil MED-6300 silicone filling.

Figure 6:
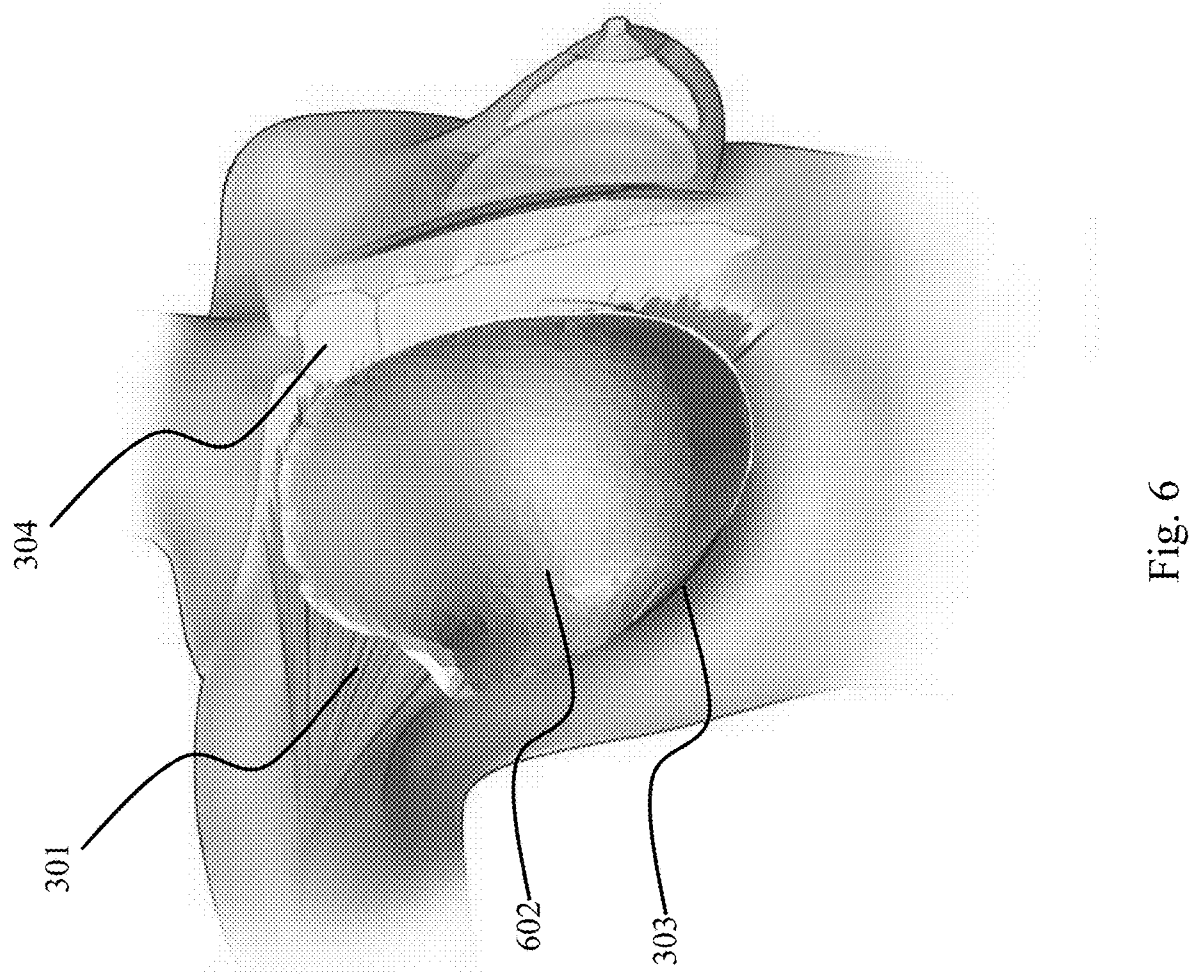
FIG. 6 is an illustration of an implanted breast implant.

A graphical representation of an implant is shown in FIG. 6. Implant 602 is positioned under the skin 303, but on top of pectoral muscle 301 and ribcage 304, but because implant 602 was made with the disclosed method, it provides a much better aesthetic fit than a standard size implant. In one embodiment, the implant is configured to contour to the ribcage and/or the pectoral muscle on the back side, expand upward toward the clavicle-collarbone, and expand inward toward the middle of the sternum.

Figure 7:
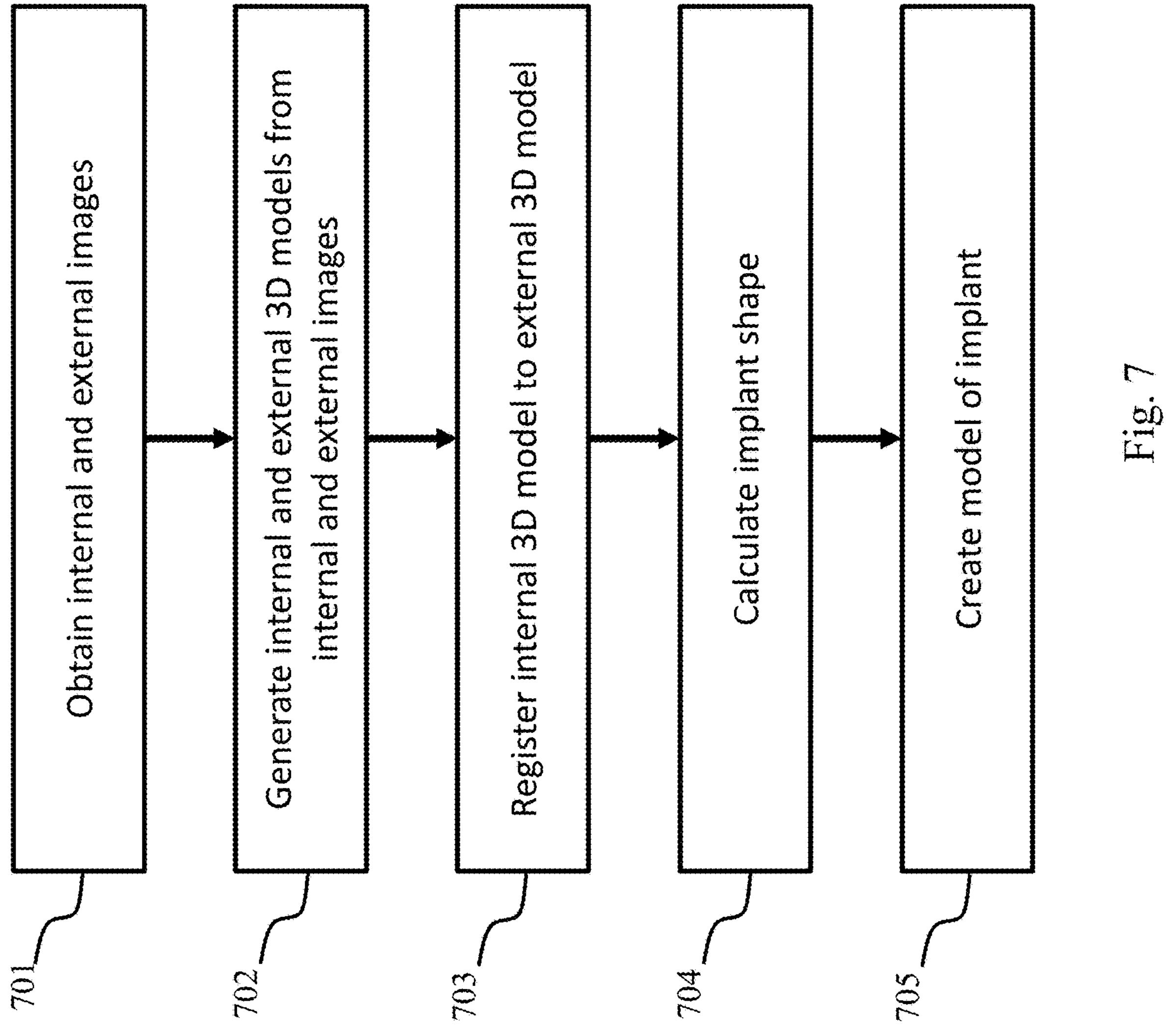
FIG. 7 is an exemplary method of designing an implant.

With reference to FIG. 7, an exemplary method of designing an implant for a subject is shown. The method comprises the steps of obtaining internal and external images of a subject in step 701, generating internal and external three-dimensional models of the subject from the internal and external images, respectively, in step 702, registering the internal 3D model to the external 3D model using an anatomical landmark in step 703, calculating the implant shape in step 704, and creating a three-dimensional model of the implant in step 705.

Another aspect of the present disclosure relates to using alginate hydrogel as a novel material for breast implants, for patients after unilateral (UM) or bilateral (BM) treatment. The disclosed materials are focused on a comparison of the Young's Modulus of commercial silicone breast implant gel and alginate hydrogels. In some embodiments, alginate hydrogels may be used in an implant alone. In other embodiments, alginate hydrogels may be used in a mixture or sandwich structure with silicone or other materials.

In some embodiments, a method of designing an implant for a subject may include additionally calculating one or more characteristics of a tissue volume extracted during a mastectomy, for example the weight of the mastectomy specimen in the operating room and the pathology lab, size of the mastectomy specimen (length, width, depth), etc. of one or more mastectomy specimens. In some embodiments, the characteristics of the resected breast tissue may be used to verify or modify the design of the breast implant for the subject from which the mastectomy specimens were removed, for example to adjust a density or volume of an implant to be closer to a density or volume of tissue removed during a mastectomy. In some embodiments, the one or more characteristics of the tissue volume may be used to validate or modify one or more models designed to approximate or duplicate a native breast, and used to design future implants, for example to validate a calculated volume, density, or shape of a breast implant calculated by a model using as its inputs only parameters discussed elsewhere in the disclosure. Exemplary input parameters include, but are not limited to, one or more MRI images, one or more ultrasound images, one or more x-ray images, or any other medical images provided to the model.

In some embodiments, a method of designing an implant for a subject may include interconnecting one or more layers with DICOM and one or more three-dimensional image format (e.g. OBJ or STL) files to one another, for example such that the layers in the files and/or the files themselves are dependent on one another. The interconnection and/or referencing of the different image files to one another allows for the creation of personalized implants, and constitutes one unique aspect of the present disclosure. Shape analyses and calculated geometries disclosed herein may be presented in some embodiments in three-dimensional image formats as contemplated herein. As contemplated herein, any of the imaging or measurement methodologies disclosed herein may be used alone or in combination to create the DICOM, OBJ, STL, or any other imaging file format disclosed herein for use with methods of the disclosure.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

Example #1—Making Silicone Breast Implants by 3D Printed Breast Molds

In this example, a mandrel of the breast shape was made by PDMS. The printed mold was used to make a PDMS mandrel for the breast shape, after that MED-6400 silicone gel was used to make the coating, and finally MED3-6300 silicone gel was used to fill the breast implant.

PDMS was mixed by mixing ratio 10:1 the base to curing agent by volume. The total volume of the breast shape was about 36 ml. A 30-minute vacuum was applied after the 10 minutes hand mixing of the PDMS. A 1 mL syringe was used to fill the mold. After that, the mold was placed into an oven under the temperature of 50 degrees Celsius for 5 hours to cure the PDMS. The glass transition temperature of PLA is between 60 to 65 degree Celsius, so the curing temperature must be below 60 degree Celsius otherwise the PLA mold will start to melt during the cure.

When filling the mold with a syringe, the base mold is filled first without the upper mold attached, and filled slowly to make sure no bubbles were attached to the wall. When the water level approaches to the maximum limit, the upper mold was added. It is also recommended to use materials like plasticine to seal the mold to prevent leakage. The design of the upper mold also must include an air hole.

In the next step, a MED-6400 coating is added to the PDMS. This procedure was done within a hood because MED-6400 has a solvent of xylene, which is organic. The amount of MED-6400 used was about 30 ml in total; this amount can be increased in order to increase the thickness of the coating, with a mixing ratio 1:1, Part A to Part B by weight. After mixing by hand for 5 to 10 minutes, a 20-minute or less vacuum was applied to remove bubbles, and after vacuuming, a thick foam of bubbles was left on top. The foam layer disappeared during the coating process. A glass beaker and a glass stirring stick was used. A set up of the mandrel is necessary to apply the coating. The coating process used pouring rather than dipping.

The curing temperature of MED-6400 has three phases. First, the material was held for 30 minutes under 25 degree Celsius, which was considered as room temperature in this work. Second, the oven temperature was increased to 75 degrees Celsius for 45 minutes. Third, the oven temperature was increased to 150 degrees Celsius for 135 minutes.

During the pouring coating process, the MED-6400 silicone gel became more and more viscous because of the curing. It is recommended to pour the gel as many times as possible to create a uniform and thick coating. Also, adding the solvent of xylene into the MED-6400 might help to delay the time of becoming viscous and reduce the appearance of bubbles.

After a strong coating was made, the filling was made. MED3-6300 silicone gel was mixed by ratio 3:1 from part A to part B. The total weight was about 40 ml. After mixing by hand for 15 minutes, a less than 10 minute vacuum was applied to remove the bubbles. A glass stirring rod was used to lead the gel into the coating when filling it. The position of the coating is the key to make sure the implant is filled. It might take some time to find the best position to fill the coating and to decide the coating openings when peeled off from the PDMS. After filling the coating, the sample was placed into the oven and it was cured under 140 degree Celsius for 5 hours. In the end, MED-6400 was used to seal the coating.

In other embodiments, a mandrel may be made by CNC machining and the coating process may implement dipping to maintain the viscosity of MED-6400 by xylene.

Example #2—Different Materials for Breast Implants

Thirty-four research papers discussing mechanical properties of the human breast, and all collected papers were reviewed to find a range of Young's Moduli for healthy breast tissues and benign breast lesions. From these research papers, 20 research papers showed the Young's Modulus numbers for human breast tissues. The geography and the method were recorded. Methods were categorized into medical methods and mechanical methods. A medical method refers to an elastography method, and a mechanical method refers to a finite element method (FEM) and/or indentation test method. The categorization of results was made according to the study results. Most research papers gave a general result for the Young's Modulus on benign breast tissue, a few research papers gave the results for glandular tissue.

More than half of the Young's Moduli from the research papers were measured by the SWE elastography method. As for the mechanical method, an ex vivo indentation test was done on a breast sample to get the Young's Modulus from one research paper. Another research paper was using FEM to do the simulation on a breast model, and the Young's Modulus used in FEM was referenced.

The Young's Modulus of skin tissue (12 KPa) was only given by one source. The Young's Modulus for glandular tissue ranged between 2 and 45 KPa. The Young's Modulus of fat tissue ranges between 0.5 and 25 KPa. The Young's Modulus of fat and fibroglandular (FEG) tissue ranges from 20.9 to 26.3 KPa. The results from mean benign tissue (such as benign tissue in the area of a breast tumor) ranged from 3.07 to 939 KPa.

Young's Modulus values were compared with commercial silicone gels and alginate hydrogels. Four MED-6400 and MED3-6300 silicone gel samples were made to find the Young's Modulus value. Four sandwich structures were made of MED-6400 and MED3-6300 silicone gels. Three alginate hydrogel samples for 1% wt, 2% wt and 3% wt were made for an indentation test.

Methods and Materials

Medical grade silicone gels MED3-6300 and MED-6400 were used MED-6400 silicone gel was used as the coating for commercial breast implants, and MED3-6300 silicone gel was used as the filling. Following the chemical procedure, the sandwich structure samples were made with MED-6400 and MED3-6300 silicone gel. An indentation test was also done on the sandwich and MED-6400 silicone gel samples. Rheometric tests were done on MED3-6300 silicone gel samples.

Alginate hydrogel samples were made by using sodium alginate solution and calcium chloride solution. 1% wt, 2% wt and 3% wt sodium alginate solutions were made by dissolving sodium alginate powder into distilled water. 1 molar calcium chloride solution was made from dissolving calcium chloride powder into distilled water. Small aluminum baking cups were used as the mold for all samples.

An INSTRON 5566 indentation machine was used for indentation test. This machine recorded the applied load and the transducer's traveling distance corresponding with time. The machine has a maximum load of 10000 N and the transducer loading rate was 0.08 mm/s. The stress of the material at each second can be calculated from the raw data. For the indentation tests in this study, only elastic properties of the samples were studied.

The transducer of the rheometer used in the rheometric test had a diameter of 13 mm. A vacuum drying oven was used to remove air bubbles. A weight scaler was used to record the weight of each material, and a lab oven was used to cure silicone gels.

Preparation of Samples

The MED3-6300 silicone gel includes part A and part B, and the mixing ratio used was 3:1, part A (50.4 g) to part B (16.8 g). The curing condition was 140 degrees Celsius for 5 hours. The 3:1 liquid was mixed manually with a stirring rod for 15 minutes. Four aluminum mini baking cups were put into the vacuum drying oven for 10 minutes to remove bubbles from the mixture. The vacuum pressure was about 60 cmHg. The cured MED3-6300 silicone gel acts like a liquid.

MED-6400 silicone gel was mixed in a mixing ratio 1:1, part A (35 g) to part B (35 g). The curing process for MED-6400 has three steps, first step is under 25 degree Celsius for 30 minutes, second step is under 75 degree Celsius for 45 minutes and the third step is under 150 degree Celsius for 135 minutes. Samples were vacuumed for 20 minutes under a pressure of about 60 cmHg before the third curing step.

The sandwich structure was made by placing MED3-6300 silicone gel in the bottom as the first layer. After curing the first layer and waiting the samples to cool down; the second thinner layer of uncured MED-6400 silicone gel was added, following the process of curing the MED-6400 layer.

For alginate hydrogels three samples were made from 1% wt, 2% wt and 3% wt sodium alginate dissolved in distilled water. 2 g sodium alginate powder was used to make the 1% wt sodium alginate solution. 4 g sodium alginate powder was used to make 2% wt sodium alginate solution. 2.4 g sodium alginate powder was used to make the 3% wt sodium alginate solution. Sodium alginate solutions were placed on a magnetic stirrer overnight. In order to distinguish the different concentrations of sodium alginate solutions, 1 ml of food dye was added into the sodium alginate solutions. One molar $CaCl_2$ (Calcium chloride) solution was made by dissolving 27.74 g $CaCl_2$ powder into distilled water.

Mechanical Tests on Samples

An indentation test was conducted on the MED-6400, sandwich structure, and alginate hydrogel samples. Because of the liquid like physical property of the MED3-6300 silicone gel, the rheometric test was selected. All tests were done at room temperature which was about 25 degrees Celsius. For silicone gel and alginate hydrogel samples, samples were removed from the mold prior to the test. For sandwich structure samples, the test was done without removing the mold.

The indentation test consisted of placing the sample on the center of a platform, where a computer automatically records the distance and force graph when the sample surface is in complete contact with the indentation tool. In order to control the result, the same indentation transducer with a diameter of 13 mm was used for the MED-6400, sandwich structure, and alginate hydrogel samples.

In the experimental work of MED3-6300, in order to control the test result, the weight of each tested sample was controlled to be the same, and the gap between the transducer and the platform was also controlled to be the same, (about 6.8 mm) for each test.

The novel approach in this experimental work was to control the crosslink process by spraying calcium chloride solution onto the sodium alginate solution surface. After spraying $CaCl_2$ solution, the samples were set overnight for homogeneous results.

Results

Figure 8A:
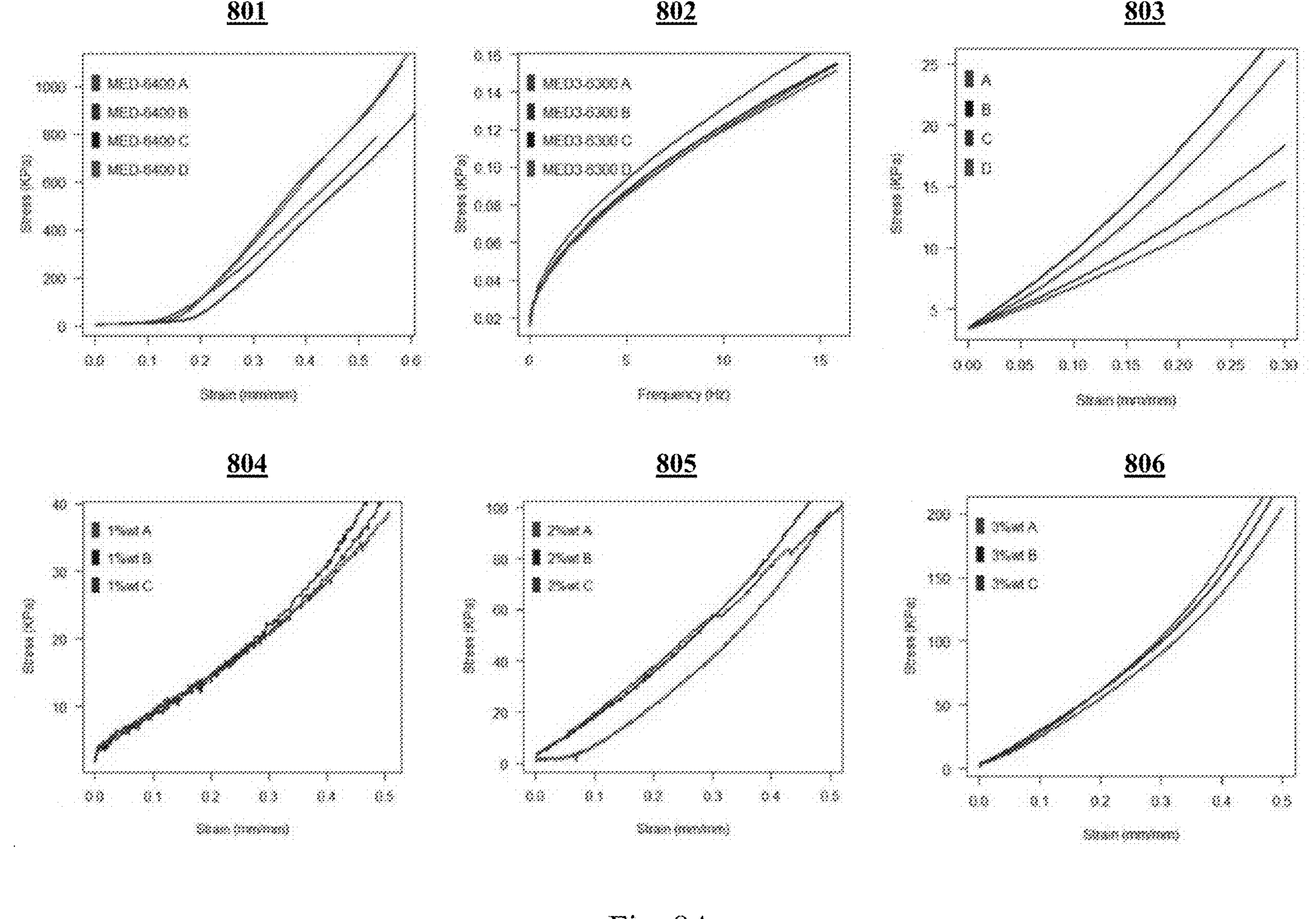
FIG. 8A and FIG. 8B are graphs of experimental data.

The elasticity of MED-6400 silicone gel was as high as about 1000 KPa as shown in graph 801 of FIG. 8A, and the mean elasticity was calculated as 768±53.3 KPa. MED3-6300 silicone gel had the lowest elasticity of 0.16 KPa and the mean elasticity was 0.16±0.004 KPa, which can be observed in graph 807 in FIG. 8B. The sandwich structure exhibited an elasticity of about 30 KPa and a mean elasticity of 30±4.6 KPa. For alginate hydrogels, it was observed that the concentration of sodium alginate affects the final product's Young's Modulus. The elasticity of 1% wt alginate hydrogels was the lowest at about 40 KPa and the mean value was 42±2.4 KPa. The elasticity value for 2% wt alginate hydrogels was about 100 KPa and the mean value was 103±5.4 KPa. 3% wt alginate hydrogels had the highest Young's Modulus value of 200 KPa and the mean value was 225±10.3 KPa. Comparing with a glandular tissue Young's Modulus value of between 2 KPa and 45 KPa, 1% wt alginate hydrogel was identified as the optimal material for the next phase of this study, for it has the closest elasticity value to the glandular tissue. It can also be observed that the sandwich structure silicone gel had a Young's Modulus close to alginate hydrogels. In graph 808 of FIG. 8B, the sandwich structure mean stress-strain curve was overlapped with the 1% wt alginate hydrogel mean curve.

With reference to FIG. 8A, graph 801 shows a stress-strain diagram for MED-6400 silicone gel samples. Graph 802 shows a rheometer diagram for MED3-6300 silicone gel samples. Graph 803 shows a stress-strain diagram for sandwich structure samples. Graph 804 shows a stress-strain diagram for 1% wt alginate hydrogel samples. Graph 805 shows a stress-strain diagram for 2% wt alginate hydrogel samples. Graph 806 shows a stress-strain diagram for 3% wt alginate hydrogel samples.

Figure 8B:
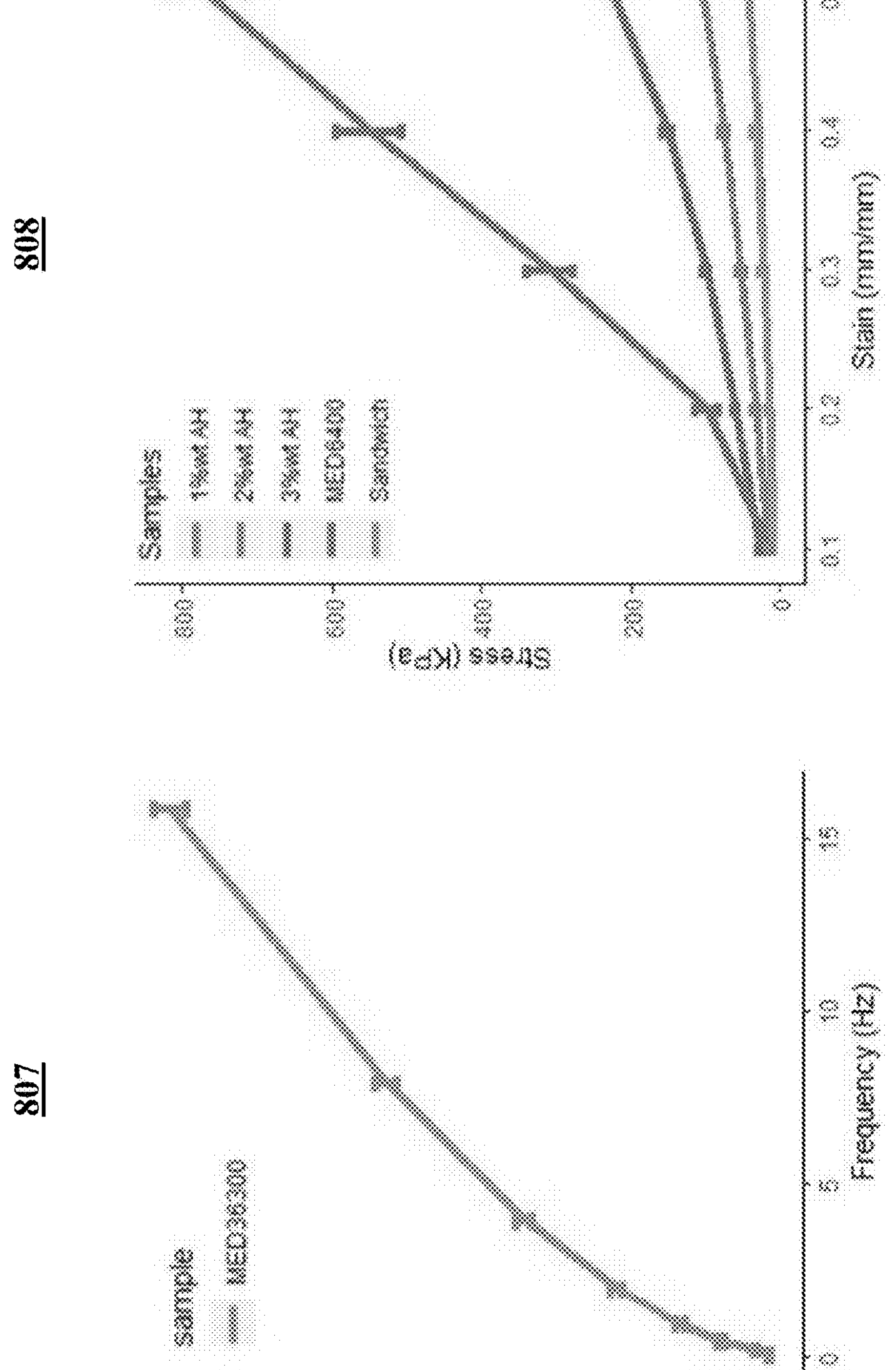

With reference to FIG. 8B, graph 807 shows a mean rheometer diagram with error bars for MED3-6300 silicone samples. Graph 808 shows the mean stress-strain diagram with error bars for MED-6400 silicone gels, alginate hydrogels and sandwich structures.

MED-6400 silicone gel samples had the highest Young's Modulus value. This is because MED-6400 silicone gel was designed to be used as a coating for SIs. A high Young's Modulus value can prevent it from breaking or being torn open when the silicone implant moves inside the human body. For MED3-6300, this silicone gel was designed to be soft and liquid-like. In the former generation SIs were made of solid alloplastic materials, which tended to develop major capsular, breast firmness and distortion of the breast.

CONCLUSION

In order to find an advantageous material as a novel solution for BC patients, the Young's Moduli of alginate hydrogels were studied. At the same time, the Young's Modulus of commercial silicone gel was used as reference to compare it with alginate hydrogels. The reason for using Young's Modulus as a reference number is because the elasticity corresponds to the stiffness of the material, and in commercial breast implants, this value was used to correspond to softness. Because alginate hydrogels can act as a scaffold for cells, a material with a similar Young's Modulus can also provide similar results in softness. It is also considered that a crosslinked scaffold with a similar elasticity might have a better porosity for specific cells. In implementations involving 3D printed bone implants, selection of a material with a similar Young's Modulus helps bone cells to grow within the implant and eventually the implant becomes integrated with the original bone. This effect is one objective of the present disclosed devices and methods, in that an ideal personalized breast implant is able to integrate with breast tissue.

The reported tensile strength of the MED-6400 used in the disclosure was 11.3 MPa. The manufacturer's test was performed according to the ASTM D412 standard. In the indentation test performed for the disclosed experimental example, the elasticity was measured at up to about 1000 KPa for the test, which was not trying to find the ultimate tensile strength for the material. The result also showed that 1% wt alginate hydrogel can be considered as a potential material for future research, which is making personalized breast implants using alginate hydrogels and culturing fat cells on alginate hydrogels.

The disclosed experimental example included the following limitations: During the process of making alginate hydrogels, the amount of sprayed Calcium Chloride was not able to be measured accurately. Additionally, there were no available reference values for elasticity of alginate hydrogel samples based on indentation tests, and so it was not possible to judge the accuracy of the disclosed measured values against similar measurements made by third parties.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for designing an implant for a subject, comprising:

generating an internal three-dimensional model of an internal anatomy of the subject from at least one internal image of the internal anatomy of the subject, the at least one internal image comprising at least one internal view of an anatomical landmark;

generating an external three-dimensional model of a surface of the subject from at least one surface image of the surface of the subject, the at least one surface image comprising at least one external view of the anatomical landmark;

registering the internal three-dimensional model to the external three-dimensional model with the anatomical landmark to create a unified three-dimensional model of the subject;

identifying an internal anatomical geometry of the subject from the internal three- dimensional model and an external anatomical geometry of the subject from the external three- dimensional model;

calculating an implant shape and volume based on a difference between the internal geometry and the external geometry in the unified three-dimensional model; and creating a three-dimensional model of an implant having the calculated implant shape and volume;

wherein the implant is a breast implant, and wherein the at least one internal view comprises the pectoralis major.

2. The method of claim 1, wherein the method further comprises the steps of: segmenting the pectoralis major; and calculating a thickness of the pectoralis major.

3. The method of claim 1, wherein the anatomical landmark is selected from the group consisting of the sternum, the suprasternal notch, and a side of a ribcage.

4. The method of claim 1, wherein the breast implant is selected from a prepectoral breast implant or subpectoral breast implant.

5. The method of claim 1, wherein the at least one internal image is generated by a method selected from the group consisting of MRI, X-Ray, and Ultrasound.

6. The method of claim 1, wherein the at least one surface image is generated by a method selected from the group consisting of a 3D scanner, stereoscopic imaging, millimeter-wave imaging, and infrared imaging.

7. The method of claim 1, further comprising the step of creating the implant with an additive manufacturing process.

8. The method of claim 1, further comprising the steps of:

creating a three-dimensional model for a mold from the calculated implant shape; and building the mold from the three-dimensional model; and forming the implant with the mold.

9. The method of claim 8, wherein the mold is built using an additive manufacturing process.

10. The method of claim 8, further comprising the steps of forming a replica of the implant with the mold; and forming the implant from the replica.

11. The method of claim 8, wherein the implant comprises a first material, and the method further comprises the step of coating the implant with a second material different from the first material.

12. The method of claim 1, further comprising the step of creating the implant, wherein the implant comprises an alginate hydrogel.

13. The method of claim 12, wherein the alginate hydrogel is selected from a 1% wt alginate hydrogel or an alginate hydrogel comprising sodium alginate.

14. A system for designing an implant for a subject, comprising a computing device comprising a non-transitory computer-readable medium with instructions stored thereon, which when executed by a processor perform steps comprising:

generating an internal three-dimensional model of an internal anatomy of the subject from at least one internal image of the internal anatomy of the subject;

generating an external three-dimensional model of a surface of the subject from at least one surface image of the subject; wherein the at least one surface image is generated by a method selected from the group consisting of a 3D scanner, stereoscopic imaging, millimeter-wave imaging, and infrared imaging:

registering the internal three-dimensional model to the external three-dimensional model with an anatomical landmark present in the internal three-dimensional model and the external three-dimensional model to create a unified three-dimensional model of the subject;

identifying an internal anatomical geometry of the subject from the internal three-dimensional model and an external anatomical geometry of the subject from the external three-dimensional model;

calculating an implant shape and volume based on a difference between the internal geometry and the external geometry in the unified three-dimensional model; and creating a three-dimensional model from the of an implant having the calculated implant shape and volume.

15. The system of claim 14, wherein the three-dimensional model is a three-dimensional model for a mold.

16. The system of claim 14, wherein the implant is a breast implant.

17. The system of claim 14, wherein the at least one internal image is generated by a method selected from the group consisting of MRI, X-Ray, and Ultrasound.

* * * * *